(12) United States Patent
Iversen et al.

(10) Patent No.: US 10,113,570 B2
(45) Date of Patent: Oct. 30, 2018

(54) SYSTEM AND METHOD FOR IN-SITU STATE MONITORING OF A HYDRAULIC SYSTEM

(71) Applicant: Mera AS, Haugesund (NO)

(72) Inventors: Erling Iversen, Sveio (NO); Dennis Frønsdal, Sveio (NO)

(73) Assignee: Mera AS, Haugesund (NO)

( * ) Notice: Subject to any disclaimer, the term of this patent is extended or adjusted under 35 U.S.C. 154(b) by 65 days.

(21) Appl. No.: 15/302,266

(22) PCT Filed: Apr. 9, 2015

(86) PCT No.: PCT/NO2015/050065
§ 371 (c)(1),
(2) Date: Oct. 6, 2016

(87) PCT Pub. No.: WO2015/156681
PCT Pub. Date: Oct. 15, 2015

(65) Prior Publication Data
US 2017/0030383 A1 Feb. 2, 2017

(30) Foreign Application Priority Data
Apr. 11, 2014 (NO) .................................. 20140477

(51) Int. Cl.
*G06F 19/00* (2018.01)
*F15B 19/00* (2006.01)
(Continued)

(52) U.S. Cl.
CPC .......... *F15B 19/005* (2013.01); *F15B 21/045* (2013.01); *G01N 33/28* (2013.01);
(Continued)

(58) Field of Classification Search
CPC .......... A61B 5/412; A61B 5/415; A61B 5/418
(Continued)

(56) References Cited

U.S. PATENT DOCUMENTS 4,947,468 A 8/1990 Nelson
5,968,371 A 10/1999 Verdegan et al.
(Continued)

FOREIGN PATENT DOCUMENTS

CN 103541951 1/2014
CN 103616835 3/2014
(Continued)

OTHER PUBLICATIONS

International Search Report, PCT/NO2015/050065, dated Aug. 6, 2015.
(Continued)

*Primary Examiner* — Edward Raymond
(74) *Attorney, Agent, or Firm* — Andrus Intellectual Property Law, LLP

(57) ABSTRACT

A monitoring system is for in-situ monitoring of a state of a hydraulic system. A hydraulic fluid inlet is coupled to the hydraulic system. A hydraulic fluid outlet is coupled to the hydraulic system. A hydraulic circuit is between the inlet and the outlet. A sensor unit is in the hydraulic circuit. The sensor unit is configured for measuring at least one property of the hydraulic fluid within the hydraulic circuit in operational use of the monitoring system. A processor unit reads out at least one output of the at least one sensor unit and determines a condition of the hydraulic fluid running through the hydraulic circuit. The processor unit determines a representative of a state of the hydraulic system based upon the condition of the hydraulic fluid and is coupled to a display device for displaying the representative.

20 Claims, 4 Drawing Sheets

(51) Int. Cl.
  *G01N 33/28* (2006.01)
  *G08B 21/18* (2006.01)
  *F15B 21/04* (2006.01)
(52) U.S. Cl.
  CPC .... *G08B 21/182* (2013.01); *F15B 2211/6303* (2013.01); *F15B 2211/6343* (2013.01); *F15B 2211/857* (2013.01)
(58) Field of Classification Search
  USPC .......................................... 702/50, 182–185
  See application file for complete search history.

(56) References Cited

U.S. PATENT DOCUMENTS

| | | | |
|---|---|---|---|
| 6,282,947 | B1 | 9/2001 | Schon et al. |
| 7,891,234 | B2 | 2/2011 | Le et al. |
| 2005/0288848 | A1 | 12/2005 | Ha |
| 2009/0107291 | A1 | 4/2009 | Douglas |
| 2009/0192728 | A1 | 7/2009 | Wright et al. |
| 2009/0312963 | A1 | 12/2009 | Najim Al-Khamis |
| 2010/0083730 | A1 | 4/2010 | Le et al. |
| 2010/0102974 | A1 | 4/2010 | Keast et al. |
| 2011/0282631 | A1 | 11/2011 | Poling et al. |
| 2013/0211797 | A1* | 8/2013 | Scolnicov .......... G06Q 10/0639 703/2 |

FOREIGN PATENT DOCUMENTS

| | | |
|---|---|---|
| DE | 102011121528 | 6/2013 |
| GB | 2396693 | 6/2004 |
| NO | 20101032 | 1/2012 |
| RU | 2005115346 | 11/2006 |
| RU | 2008111643 | 10/2009 |
| RU | 2010112713 | 10/2011 |

OTHER PUBLICATIONS

PCT Written Opinion, PCT/NO2015/050065, dated Aug. 6, 2015.
Norwegian Search Report, Norwegian Patent Application No. 20140477, dated Oct. 22, 2014.
International Preliminary Report on Patentability, PCT/CN02015/050065, date of completion Apr. 11, 2016.

* cited by examiner

SYSTEM AND METHOD FOR IN-SITU STATE MONITORING OF A HYDRAULIC SYSTEM

CROSS-REFERENCE TO RELATED APPLICATIONS

This application is the U.S. national stage application of International Application PCT/NO2015/050065, filed Apr. 9, 2015, which international application was published on Oct. 15, 2015, as International Publication WO 2015/156681 in the English language. The International Application claims priority of Norwegian Patent Application No. 20140477, filed Apr. 11, 2014. The international application and Norwegian application are both incorporated herein by reference, in entirety.

FIELD OF THE INVENTION

The invention relates to a monitoring system for in-situ monitoring of a state of a hydraulic system. The invention further relates to a method for in-situ monitoring of a state of a hydraulic system.

BACKGROUND OF THE INVENTION

Different methods of monitoring the condition of hydraulic systems have been reported. Condition monitoring of hydraulic oil systems is possible by several methods. Among them are techniques such as visual inspection, temperature monitoring, vibration analysis and oil analysis. Oil analysis indicates the cleanliness of the oil and physical properties. By carrying out oil analysis, the condition of the hydraulic oil can be determined. Subsequently by proper interpretation of the determined condition of the hydraulic oil, the condition of the hydraulic system, from which the oil sample was taken, may be determined as well.

Common practice for oil condition monitoring is based on oil sampling from designated sampling points at given time intervals. The time interval will change as the operational mode changes and can vary from hours to weeks. Oil samples are then sent to a laboratory for examination, and the end user will receive the result in form of an analysis report.

This known method has several main disadvantages. The first disadvantage is that it is time consuming, as it will take days to receive the result of the oil analysis from the laboratory. The second disadvantage is that a lot of knowledge of the hydraulic system is required in order to correctly interpret the meaning of the analysis results in the analysis reports. Quite often personnel conducting the examination has little knowledge about the meaning of the analysis results, because such interpretation does not form part of the daily operation of the relevant hydraulic oil system. The third disadvantage is that the taking of oil samples is challenging in terms of repeatability. This is caused by the high sensitivity of the oil analysis towards contamination. Expressed differently, the level of cleanliness of the sample container has a large impact on the oil analysis results.

US2011/0282631A1 discloses a fluid analyzing system wherein an electronic control module is coupled with an asset (comprising a hydraulic system) and a telematics device. The electronic control module initiates the acquisition of a sample of an asset's fluid and analyses the sample in response to an analysis trigger. An asset management system located remotely from the asset and telematics device receives the results of the fluid analysis wirelessly via the telematics device.

SUMMARY OF THE INVENTION

The invention has for its object to remedy or to reduce at least one of the drawbacks of the prior art, or at least provide a useful alternative to prior art.

The invention is defined by the independent patent claims. The dependent claims defines advantageous embodiments of the invention.

The object is achieved through features, which are specified in the description below and in the claims that follow.

The effects of the combination of the features of the invention are as follows. First of all, the monitoring system is coupled to a hydraulic system such that, in operational use of the hydraulic system, the hydraulic fluid of the hydraulic system flows from the hydraulic system via the hydraulic fluid inlet to the monitoring system, and then through the hydraulic circuit of the monitoring system and then back to the hydraulic system via the hydraulic fluid outlet. Subsequently, the hydraulic fluid is properly circulated through the hydraulic circuit of the monitoring system. Within the hydraulic circuit at least one property of the hydraulic fluid is measured by the at least one sensor unit. Further, a condition of the hydraulic fluid is determined, which is indicative for a state of the hydraulic system. In addition, a representative of the state of the hydraulic system is determined based upon the condition of the hydraulic fluid. The representative may also be displayed on a display device. Thus, the invention renders it possible to monitor the state of a hydraulic system in-situ by monitoring the condition of the hydraulic fluid with sensor units, thereby rendering the taking of samples and having them analysed in a lab superfluous.

For a proper understanding of the scope of the invention, a few expressions and terms are further defined in this paragraph. In the context of the invention with the term "hydraulic circuit" is typically meant a conduction path through which the hydraulic fluid flows. Within the hydraulic circuit there may be hydraulic elements, such as a pump, a valve, a motor, an actuator/cylinder, etc. Another term for "hydraulic circuit" may also be "hydraulic line" or "hydraulic loop".

In an embodiment of the monitoring system in accordance with the invention the system further comprises a hydraulic pump provided in the hydraulic circuit. The hydraulic pump that is provided in the hydraulic circuit ensures that the hydraulic fluid is properly circulated through the hydraulic circuit of the monitoring system. Such embodiment is advantageous if there is not enough pressure gradient when connecting the monitoring system to the hydraulic system.

In an embodiment of the monitoring system in accordance with the invention the at least one sensor unit is configured for measuring at least two, preferably at least three, yet even more preferably at least four, yet even more preferably at least five, and even more preferably at least six, properties selected from a group comprising: temperature, viscosity, dielectric permittivity, relative humidity, electrical conductivity, and particle size distribution, and wherein the processor unit is configured for reading out at specific time instances respective actual property values for all measured properties. The more properties are measured of the hydraulic fluid the more precise the condition of the hydraulic fluid can be determined, and thereby a more accurate determination of the state of the hydraulic system is made possible.

In an embodiment of the monitoring system in accordance with the invention the processor unit is further configured for logging said respective actual property values at specific time instants in order to determine transient behaviour of said values. Logging the actual property values of said properties conveniently provides for information on the transient behaviour of said values.

In an embodiment of the monitoring system in accordance with the invention the processor unit is further configured for determining respective compensated property values for said respective actual property values. The actual property values of the properties of the hydraulic fluid may be susceptible to significant changes due to change of condition such as temperature, pressure, etc. Hence, there may be a need to determine so-called compensated property values for the respective properties. In one embodiment such compensated property values are temperature-normalized values, which means the value of said property at a specific temperature, for instance 40 degrees Celsius. Once the dependency of a respective property on the temperature as well as the actual temperature are known it is relatively easy to calculate the value of the property at the specific temperature.

In an embodiment of the monitoring system in accordance with the invention the processor unit is configured for determining a characteristic property value set for a specific hydraulic system by monitoring, and optionally averaging, said actual property values and/or determined compensated property values during a predefined time period. In this embodiment the monitoring system conveniently determines a characteristic property value set, for instance when the hydraulic system is used for the first time. By measuring the actual property values and/or the compensated property values and optionally averaging respective property values, which are typical for a hydraulic system being in a good state, can be determined. This then gives the characteristic property value set, which may also be referred to as the fingerprint of the hydraulic system.

In an embodiment of the monitoring system in accordance with the invention the processor unit is configured for comparing the actual property values or compensated property values with said characteristic property value set for determining a deviation between said actual property values and said characteristic property value set and for determining a duration of said deviation. The property values typically vary over time. Measuring the deviation as well as the duration of the deviation gives an indication on the condition of the hydraulic fluid and thereby also on the state of the hydraulic system.

In an embodiment of the monitoring system in accordance with the invention the processor unit is further configured for assigning a respective individual alarm indicator for each actual property value or compensated property value, wherein the individual alarm indicator is indicative for the deviation and the duration of said deviation. Assigning an alarm indicator in case the deviation between the property value and the characteristic value is too large conveniently provides for a visualisation of the condition of the hydraulic system and thereby on the state of the hydraulic system. It may be advantageous to set a certain duration threshold for each deviation threshold, which means that the respective alarm indicator is only assigned when the duration exceeds the duration threshold. Once the characteristic property value for a property is determined, it may be decided to define three different alarm indicators, for instance green, yellow and red. The green indicator may be defined as a deviation within a first limit. A yellow indicator may then be defined as a deviation larger than the first limit yet lower than a second limit higher than the first limit, and with a duration larger than 1 hour for example. Then a red indicator may be defined as a deviation larger than the second limit and with a duration larger than 2 hours for example. It must be noted that there is a numerous number of variations possible on this principle.

In an embodiment of the monitoring system in accordance with the invention the processor unit is further configured for assigning a respective overall alarm indicator for the system, wherein the overall alarm indicator is derived from the respective one or more individual alarm indicators, wherein the overall alarm indicator is indicative for overall condition of the hydraulic fluid. In particular when there is a plurality of properties with each their individual alarm indicator, it may be advantageous to define an overall alarm indicator that is indicative for the overall condition of the hydraulic fluid.

In an embodiment of the monitoring system in accordance with the invention the processor unit is further configured for assigning a respective fault-mode indicator taken from a fault-mode library, wherein specific parameter values or ranges have been assigned to certain fault-modes. In this embodiment the system is provided with more information about the relation between the condition of the hydraulic fluid and the state of the hydraulic system. Such information is provided in the form of a fault-mode library, wherein specific parameter values or ranges have been assigned to certain fault-modes (for instance: system has a leakage, system needs maintenance, for instance the form of hydraulic fluid replacement, etc). Such fault-mode library may be conveniently built by doing research and experiments. The more information is built into the system, the less knowledge is required from the operator of the hydraulic system.

In an embodiment of the monitoring system in accordance with the invention the processor unit is configured for reading out respective actual property values with a sampling rate between once-per-minute and once-per-hour, but preferably with a sample rate of once-per-five-minutes. It will be clear that the advantage of the invention for a large part resides in the in-situ measuring of the properties of the hydraulic fluid. Contrary to taking samples and having them analysed in a laboratory, the monitoring system of the invention renders such handling superfluous. This advantage is imminent at any sampling rate, yet it may be advantageous to have a sampling rate in the order of once-per hour down to once-per five minutes, for example. Such, sampling rate provides for a higher accuracy of the system, and also enables quicker fault detection and thereby allows for quicker intervention in case something is not in order with the hydraulic system.

In a second aspect the invention relates to a method for in-situ monitoring of a state of a hydraulic system. The method comprises:

coupling a monitoring system to the hydraulic system such that, in operational use of the monitoring system, hydraulic fluid of the hydraulic system flows from the hydraulic system through a hydraulic circuit of the monitoring system and back to the hydraulic system;

measuring at least one property of the hydraulic fluid within the hydraulic circuit of the monitoring system;

determining a condition of the hydraulic fluid running through the hydraulic circuit;

determining a state of the hydraulic system based upon the condition of the hydraulic fluid, and displaying a representative of the state.

The advantages and effects of the method of the invention follow that of the system of the invention. Likewise, the advantages and effects of the embodiments of the method of the invention follows those of the corresponding embodiments of the system of the invention.

In an embodiment of the method in accordance with the invention, in the step of measuring at least one property, at least the following is measured, at least two, preferably at least three, yet even more preferably at least four, yet even more preferably at least five, and even more preferably at least six, properties selected from a group comprising: temperature, viscosity, dielectric permittivity, relative humidity, electrical conductivity, and particle size distribution, wherein at specific time instances respective actual property values for all measured properties are read out.

In an embodiment of the method in accordance with the invention the method further comprises the step of logging said respective actual property values at specific time instants in order to determine transient behaviour of said values.

In an embodiment of the method in accordance with the invention the method further comprises the step of determining respective compensated property values for said respective actual property values.

In an embodiment of the method in accordance with the invention the method further comprises the step of determining a characteristic property value set for a specific hydraulic system by monitoring and averaging said actual property values or determined compensated property values during a predefined time period.

In an embodiment of the method in accordance with the invention the method further comprises the step of comparing the actual property values or compensated property values with said characteristic property value set for determining a deviation between said actual property values and said characteristic property value set and also for determining a duration of said deviation.

In an embodiment of the method in accordance with the invention the method further comprises the step of assigning a respective individual alarm indicator for each actual property value or compensated property value, wherein the individual alarm indicator is indicative for the deviation and the duration of said deviation.

In an embodiment of the method in accordance with the invention the method further comprises the step of assigning a respective overall alarm indicator for the system, wherein the overall alarm indicator is derived from the respective one or more individual alarm indicators, wherein the overall alarm indicator is indicative for overall state of the hydraulic fluid.

In an embodiment of the method in accordance with the invention the method further comprises the step of assigning a respective fault-mode indicator taken from a fault-mode library, wherein specific parameter values or ranges have been assigned to certain fault-modes.

In an embodiment of the method in accordance with the invention the method further comprises the step of reading out respective actual property values with a sampling rate between once-per-minute and once-per-hour, but preferably with a sample rate of once-per-five-minutes.

In a third aspect the invention relates to computer program product comprising instructions for causing a processor to perform the method of the invention. Even though not required at all, the method of the invention may be conveniently implemented in a computer program product (software), in part or in full.

BRIEF DESCRIPTION OF THE DRAWINGS

In the following is described an example of a preferred embodiment illustrated in the accompanying drawings, wherein.

DETAILED DESCRIPTION OF THE EMBODIMENTS

Figure 1A:
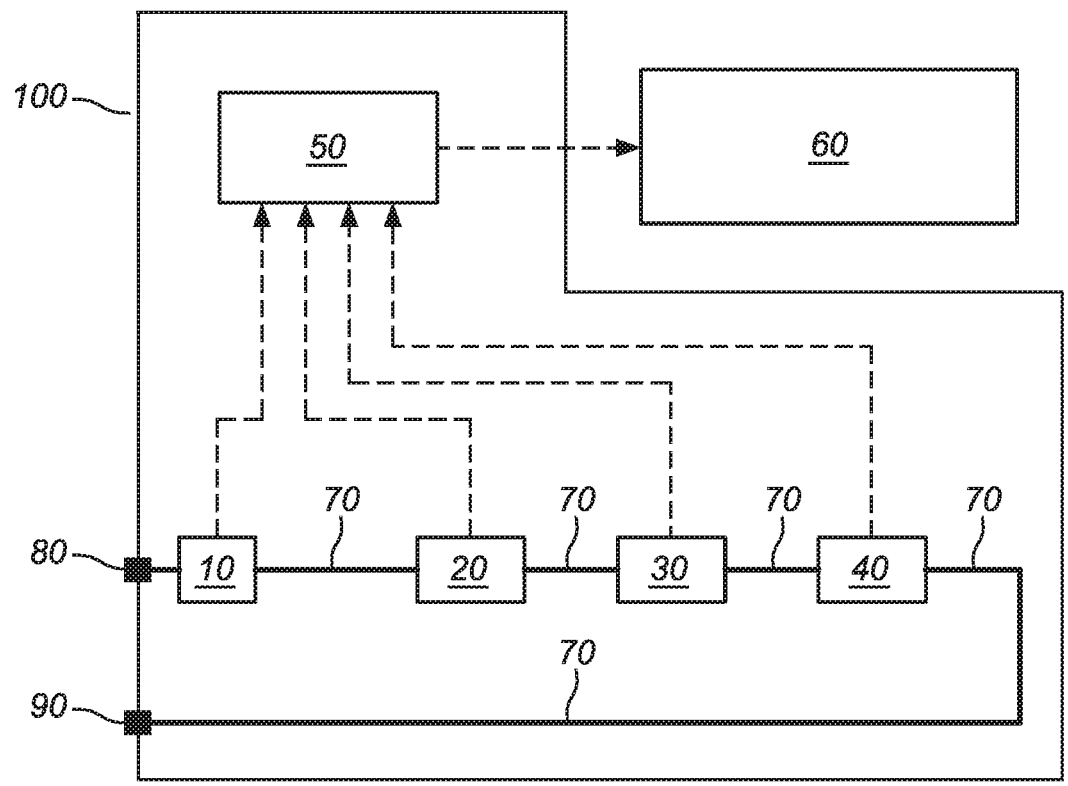
FIG. 1a shows a schematic view of the monitoring system in accordance with an embodiment of the invention.
Figure 1B:
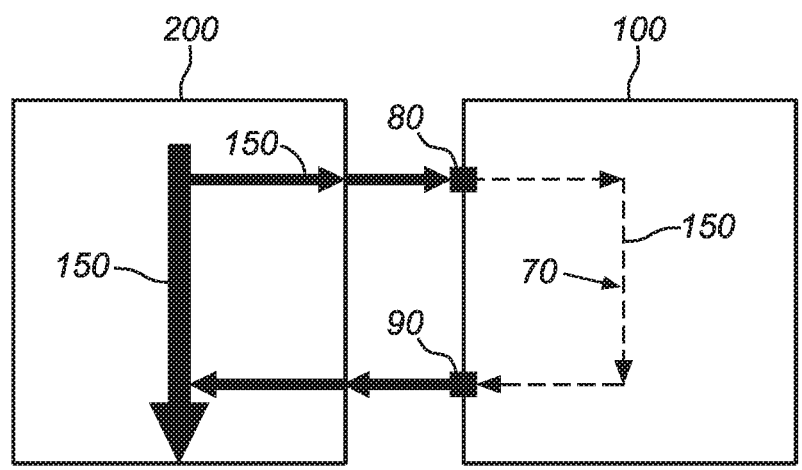
FIG. 1b shows a schematic view of how the monitoring system is connected to a hydraulic system to be monitored in operational use.

FIG. 1a shows a schematic view of a monitoring system in accordance with an embodiment of the invention. FIG. 1b shows a schematic view of how the monitoring system 100 is connected to a hydraulic system 200 to be monitored in operational use. The monitoring system 100 comprises a hydraulic inlet 80, a hydraulic outlet 90 and a hydraulic circuit 70 coupled between said inlet 80 and outlet 90. The hydraulic circuit comprises a pump 10 for circulating hydraulic fluid 150 of the hydraulic system 200 through the hydraulic circuit 70 of the monitoring system 100. Within the hydraulic circuit 70 there is further provided three sensor units 20,30,40, which each measure at least one of the earlier discussed properties of the hydraulic fluid 150, namely temperature, viscosity, dielectric permittivity, relative humidity, electrical conductivity, and particle size distribution. In an embodiment the first sensor unit 20 measures temperature and viscosity, the second sensor unit 30 measures dielectric permittivity, relative humidity and electrical conductivity, and the third sensor unit 40 measure temperature for example.

The monitoring system 100 further comprises a processor unit 50, which is coupled to the sensor units 20,30,40 and to the pump 10. The processor unit 50 is configured for carrying out all kinds of tasks, which will be explained in more detail later. The processor unit 50 may be implemented in software, in hardware or a combination of hardware and software. The processor unit 50 is further coupled to a display device 60, which may be an LCD display for example. On the display 60 various types of information may be displayed, such as the actual values of the measured properties, the compensated values of the measured properties, historical values of said properties (in graphical form for example). Furthermore, operational data and alarm indicators may be displayed. The display of information may be developed specifically for condition monitoring of the hydraulic fluid 150. The monitoring system 100 may be developed such that the sampling rate is high and thus, a much higher resolution of the condition monitoring is available compared to today's standard. The system 100 may be further configured such that it will record the condition of the hydraulic system 200 over time while it is in a good state and establish a fingerprint generated from this data. The fingerprint will then work as comparison material when checking real time values at later stages. Based on this the monitoring system 100 will be able to detect irregular values and generate alarms on fault modes in the hydraulic system.

In operational use of the monitoring system 100 the hydraulic fluid 150 of the hydraulic system 200 is circulated through the three sensor units 20,30,40 by the aid of the circulation pump 10 and returned to the hydraulic system 200. The sensor units 20,30,40 monitor the condition of the hydraulic oil 150 and send the values to the processor unit 50 (for example a CPU).

Figure 2:
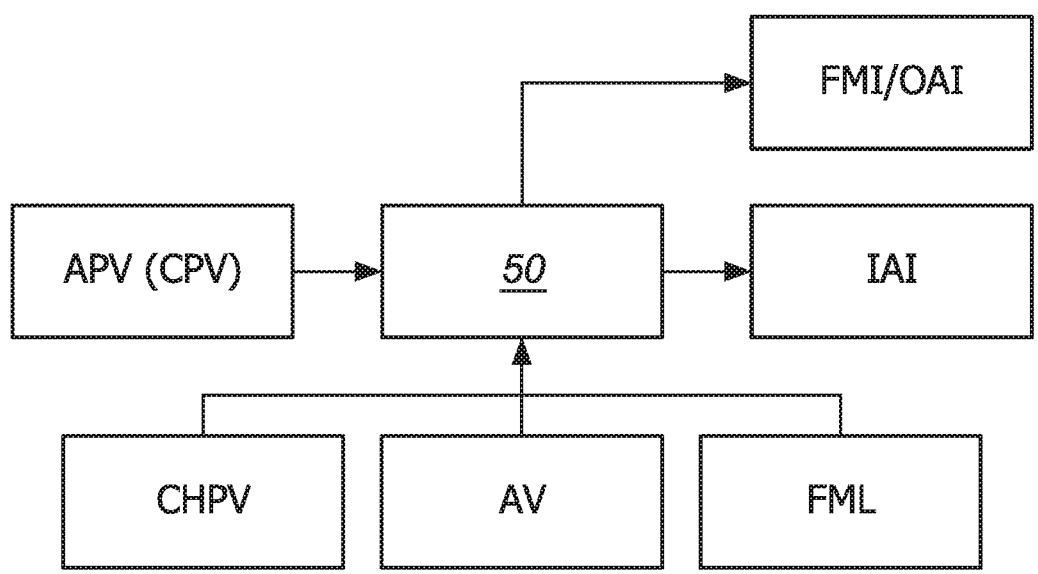
FIG. 2 illustrates some operation principles of the processor unit of the monitoring system in accordance with an embodiment of the invention.

FIG. 2 illustrates some operation principles of the processor unit 50 of the monitoring system in accordance with an embodiment of the invention. The processor unit 50 may carry out all or a selection of the following steps:

- determine and log actual property values APV and present them graphically (historical values) on the display device 60 (FIG. 1a).
- calculate and log compensated property values CPV and present them graphically (historical values) on the display device 60.
- determine a characteristic property value set (CHPV) (or fingerprint) for the hydraulic system 200 to which the monitoring system 100 is connected. This may be done by logging the values for a system that is in a good state, over time, wherein the fingerprint will be established by determining mean values and, optionally the normal change in values.
- determining the deviation between the actual property values APV and the respective characteristic property value CHPV, but also the duration of the period in which the deviation is above a predefined level (or alarm value AV).
- determining respective individual alarm indicators IAI by comparing the deviation with predefined alarm values AV and setting the respective alarm indicators IAI in case the alarm value AV has been exceed during a time period that is larger than a predefined duration period (this is effectively also an alarm value AV).
- determining an overall alarm indicator OAI derived from the individual alarm indicators IAI, which will be discussed with reference to FIG. 3.
- comparing the property values with a pre-defined fault-mode library FML, wherein specific parameter values/ranges or combinations of parameter values/ranges have been assigned to certain fault-modes. The processor unit 50 further ensures that respective fault-mode indicators FMI are presented on the display device. It must be noted that both the alarm values AV and fault mode library FML may be defined upfront for each hydraulic oil system.

Figure 3:
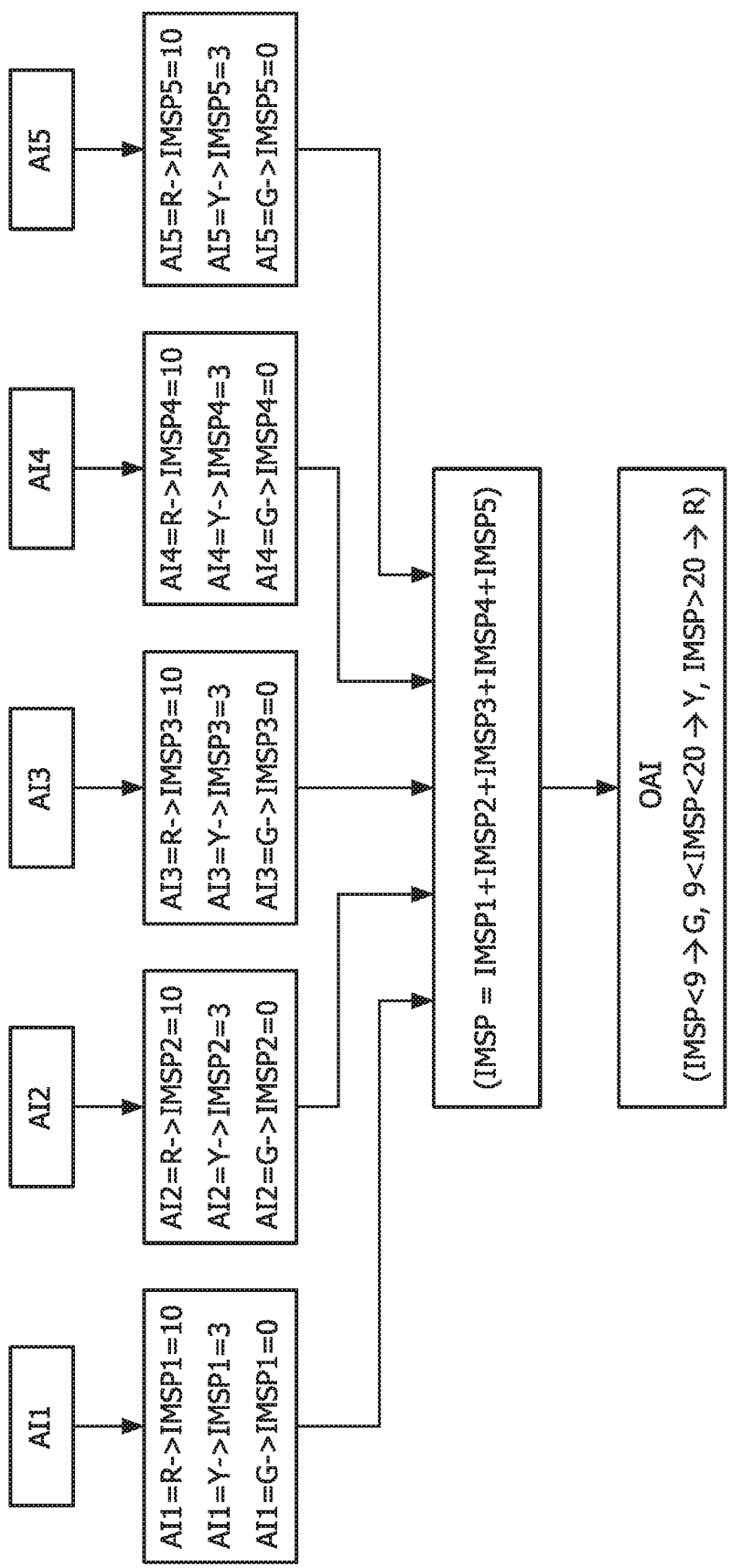
FIG. 3 illustrates a possible way of calculating an overall alarm indicator from the individual alarm indicators.

FIG. 3 illustrates a possible way of calculating an overall alarm indicator from the individual alarm indicators. Such determining may be performed by the processor unit 50 for example. It must be noted that this is just an example of determining an overall alarm indicator. In the figure there has been established respective alarm indicators AI1,AI2, AI3,AI4,AI5 for five different properties (all earlier mentioned properties except the temperature for example). In an embodiment such alarm indicators AI1,AI2,AI3,AI4,AI5 may have three different values, such as "Red" R, "Yellow" Y, and "Green" G. For each individual property a respective intermediate variable IMSP1, IMSP2,IMSP3,IMSP4,IMSP5 is subsequently defined. The value for each intermediate variable IMSP1,IMSP2,IMSP3,IMSP4,IMSP5 is determined in accordance with the "value" of the respective alarm indicator AI1,AI2,AI3,AI4,AI5 as illustrated in the figure. Subsequently, the sum IMSP of the respective intermediate variables is calculated. Finally, the overall alarm indicator OAI is determined, which may be done similar to how the individual alarm indicators are determined as illustrated in FIG. 3. Hence, the value of the overall alarm indicator OAI may also be expressed in three different values, "Red" R, "Yellow" Y, and "Green" G. Obviously, the number of variations to calculation method of FIG. 3 is almost infinite.

Figure 4:
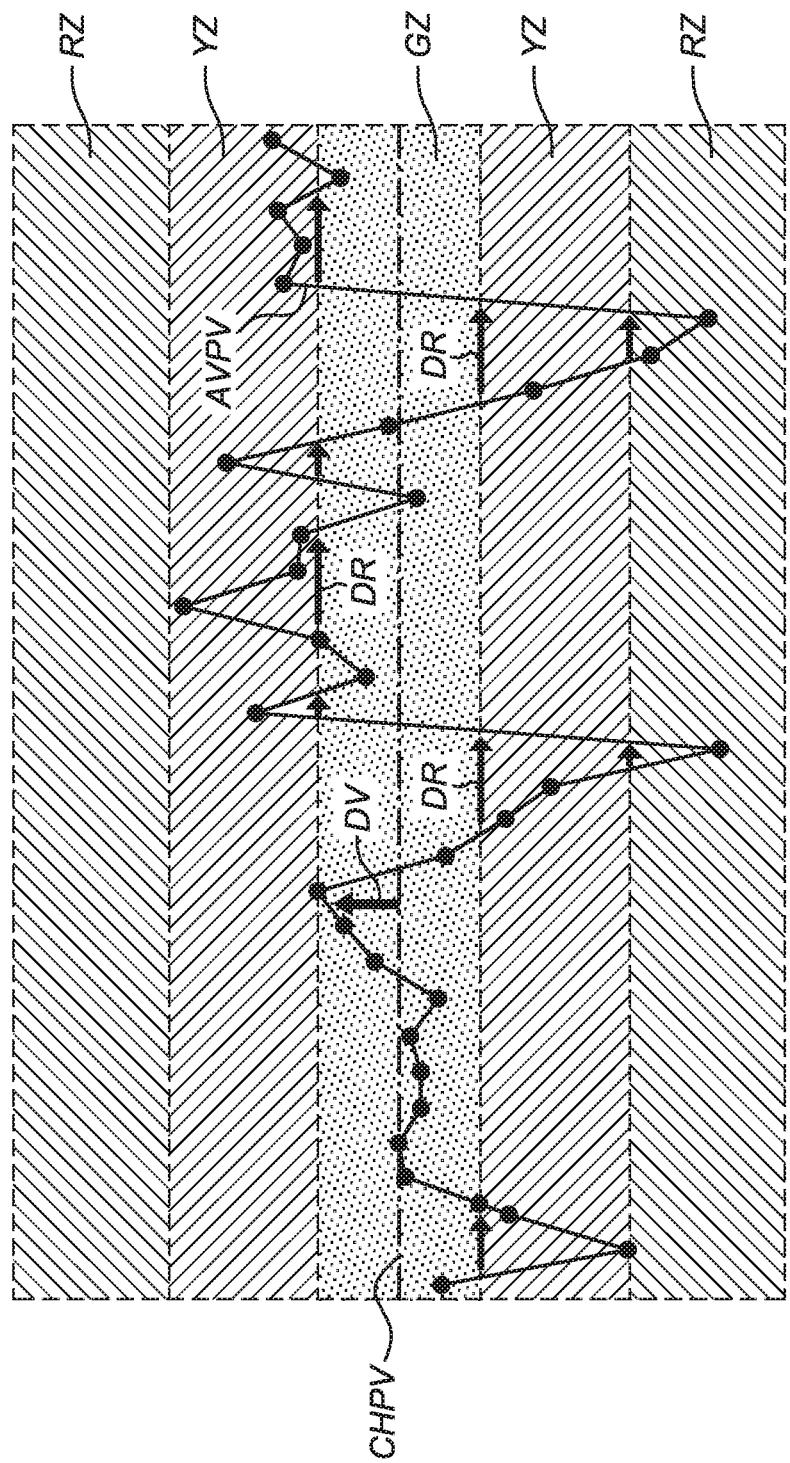
FIG. 4 shows a graph showing variations of the value of a specific property over time and how respective alarm zones for the alarm indicator may be determined for such property.

FIG. 4 shows a graph showing variations of the value of a specific property over time and how respective alarm zones for the alarm indicator may be determined for such property. The graph shows a non-compensated averaged property value AVPV over a predefined time. The figure also shows the characteristic property value CHPV. The processor unit 50 is configured to determine respective zones RZ,YZ,GZ based upon the characteristic property value CHPV and the alarm values AV that are determined for the respective hydraulic system 200. The vertical arrow in FIG. 4 illustrates the respective deviation DV between the actual (averaged) value and the characteristic value CHPV. Once the deviation DV exceeds a certain alarm value such that the value enters the yellow zone, the duration DR of this event is monitored as illustrated by the horizontal arrows. Only when this duration DR exceeds a certain alarm value, the respective alarm indicator is set to yellow. The respective duration thresholds may be set different for each zone barrier, for instance 2 hours for the crossing of the barrier between the green zone GZ and the yellow zone YZ and 1 hour for the crossing of the barrier between the yellow zone YZ and the red zone RZ. It may be chosen that in case of an alarm indicator having a value "red" an audible and/or visible alarm goes off, for example.

Measured property values will most likely vary during the time of system operation. These variations are caused by different operational factors such as temperature, air bubbles, flow turbulence etc. Variation caused by operational condition is typically of short duration and often have noticeable transients. The IMS system main objective is to determine actual change in the measured parameter over time, caused by non-operational factors.

As has becomes clear from the claims and the discussion of the different embodiments of the invention the "representative of the state of the hydraulic system" may indicate different things. It may be a simple alarm indicator, that indicates that the condition of the hydraulic fluid is, in at least one of its properties, deviating too much from the fingerprint. But it may also be a very sophisticated state indicator that gives exact information about something being wrong and what is being wrong with the hydraulic system. Such sophisticated information may be provided in the monitoring system in the form of a fault-mode library, for example. Alternatively, it may be anything in between these two examples.

The invention has been illustrated with a few example embodiments. The following advantages or key features are applicable at least to some embodiments of the invention.

- Multi-sensor feedback to determine the hydraulic oil condition is now possible;
- Custom or tailor made display of information is possible for the oil condition presentation;
- Trends based on large amount of data (high resolution) are possible;
- Real-time condition monitoring of hydraulic oil and hydraulic oil systems is possible;
- Interpretation of oil condition data to determine fault modes of hydraulic oil systems is now possible;

Sophisticated system, able to establish the characteristic property value set or fingerprint of a hydraulic oil system being in a good state.

It will be appreciated that the invention also extends to computer programs, particularly computer programs on or in a carrier, adapted for putting the invention into practice. The program may be in the form of source code, object code, a code, intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. In addition, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage. Throughout the figures, similar or corresponding features are indicated by same reference numerals or labels.

The invention claimed is:

1. A monitoring system for in-situ monitoring of a state of a hydraulic oil system, the monitoring system comprising:
   a hydraulic oil inlet configured to couple to the hydraulic oil system;
   a hydraulic oil outlet configured to couple to the hydraulic oil system;
   a hydraulic circuit disposed between the hydraulic oil inlet and the hydraulic oil outlet, such that, during operational use of the hydraulic oil system, hydraulic oil of the hydraulic oil system flows from the hydraulic oil system via the hydraulic oil inlet to the monitoring system, and then through the hydraulic circuit of the monitoring system and then back to the hydraulic oil system via the hydraulic oil outlet;
   at least one sensor unit disposed in the hydraulic circuit, wherein the at least one sensor unit is configured for measuring at least one property of the hydraulic oil within the hydraulic circuit in operational use of the monitoring system, and
   a processor unit configured to read out at least one output of the at least one sensor unit and to determine a condition of the hydraulic oil running through the hydraulic circuit, wherein the processor unit is further configured to determine a representative of a state of the hydraulic oil system based upon the condition of the hydraulic oil and further configured to couple to a display device for displaying the representative.

2. The monitoring system as claimed in claim 1, wherein the at least one sensor unit is configured for measuring at least two properties selected from the group consisting of: temperature, viscosity, dielectric permittivity, relative humidity, electrical conductivity, and particle size distribution, and wherein the processor unit is configured for reading out at specific time instances respective actual property values for all measured properties.

3. The monitoring system as claimed in claim 2, wherein the processor unit is further configured to log the respective actual property values at specific time instants in order to determine transient behavior of the respective actual property values.

4. The monitoring system as claimed in claim 2, wherein the processor unit is further configured to determine respective compensated property values for the respective actual property values, which are temperature-normalized values, namely values that are normalized for the respective actual property values at a specific temperature.

5. The monitoring system as claimed in claim 2, wherein the processor unit is configured to determine a characteristic property value set for a specific hydraulic oil system by monitoring and averaging the actual property values or the compensated property values during a predefined time period.

6. The monitoring system as claimed in claim 5, wherein the processor unit is configured to compare the actual property values or compensated property values with the characteristic property value set and determine a deviation between the actual property values and the characteristic property value set and also configured to determine a duration of the deviation.

7. The monitoring system as claimed in claim 6, wherein the processor unit is further configured to assign a respective individual alarm indicator for each actual property value or compensated property value, wherein the individual alarm indicator is indicative of the deviation and the duration of the deviation.

8. The monitoring system as claimed in claim 7, wherein the processor unit is further configured to assign a respective overall alarm indicator for the system, wherein the overall alarm indicator is derived from one or more of the respective individual alarm indicators, wherein the overall alarm indicator is indicative for an overall condition of the hydraulic oil.

9. The monitoring system as claimed in claim 6, wherein the processor unit is further configured to assign a respective fault-mode indicator taken from a fault-mode library, wherein specific parameter values or ranges have been assigned to certain fault-modes.

10. The monitoring system as claimed in claim 6, wherein the processor unit is configured to read out the respective actual property values with a sampling rate between once-per-minute and once-per-hour.

11. A method for in-situ monitoring of a state of a hydraulic oil system, the method comprising:
coupling a monitoring system to the hydraulic oil system such that, in operational use of the monitoring system, hydraulic oil of the hydraulic oil system flows from the hydraulic oil system through a hydraulic circuit of the monitoring system and back to the hydraulic oil system;
measuring at least one property of the hydraulic oil within the hydraulic circuit of the monitoring system;
determining a condition of the hydraulic oil running through the hydraulic circuit;
determining a state of the hydraulic oil system based upon the condition of the hydraulic oil, and
displaying a representative of the state.

12. The method as claimed in claim 11, wherein in the step of measuring at least one property, at least the following is measured, at least two, properties selected from the group consisting of: temperature, viscosity, dielectric permittivity, relative humidity, electrical conductivity, and particle size distribution, wherein at specific time instances respective actual property values for all measured properties are read out.

13. The method as claimed in claim 11, the method further comprising logging the respective actual property values at specific time instants in order to determine transient behavior of the values.

14. The method as claimed in claim 11, further comprising determining respective compensated property values for the respective actual property values, the respective compensated property values being temperature-normalized values, namely values that are normalized for the respective actual property values at a specific temperature.

15. The method as claimed in claim 14, further comprising determining a characteristic property value set for a specific hydraulic oil system by monitoring and averaging the actual property values or determined compensated property values during a predefined time period.

16. The method as claimed in claim 15, further comprising comparing the actual property values or compensated property values with the characteristic property value set for determining a deviation between the actual property values and the characteristic property value set and also for determining a duration of the deviation.

17. The method as claimed in claim 16, further comprising assigning a respective individual alarm indicator for each actual property value or compensated property value, wherein the individual alarm indicator is indicative for the deviation and the duration of the deviation.

18. The method as claimed in claim 17, further comprising assigning a respective overall alarm indicator for the system, wherein the overall alarm indicator is derived from the respective one or more individual alarm indicators, wherein the overall alarm indicator is indicative for overall condition of the hydraulic oil.

19. The method as claimed in claim 16, further comprising assigning a respective fault-mode indicator taken from a fault-mode library, wherein specific parameter values or ranges have been assigned to certain fault-modes.

20. The method as claimed in claim 16, further comprising reading out respective actual property values with a sampling rate between once-per-minute and once-per-hour, but preferably with a sample rate of once-per-five-minutes.

* * * * *